(12) United States Patent
Janssen

(10) Patent No.: US 9,558,649 B2
(45) Date of Patent: Jan. 31, 2017

(54) SYSTEM AND METHOD FOR MANAGING PATIENT MONITORING ALARMS

(71) Applicant: General Electric Company, Schenectady, NY (US)

(72) Inventor: Brian Janssen, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 80 days.

(21) Appl. No.: 14/145,394

(22) Filed: Dec. 31, 2013

(65) Prior Publication Data

US 2015/0187202 A1    Jul. 2, 2015

(51) Int. Cl.
*G08B 25/00* (2006.01)
*G06F 19/00* (2011.01)

(52) U.S. Cl.
CPC ......... *G08B 25/006* (2013.01); *G06F 19/3406* (2013.01); *G08B 25/005* (2013.01)

(58) Field of Classification Search
CPC ....... A61B 5/411; A61B 5/002; A61B 5/0205; A61B 5/02455; A61B 5/746; G06F 19/3418; G06F 19/3406; G08B 21/0453; G08B 23/00; G08B 25/01; G08B 25/016; G08B 25/006

USPC .............. 340/573.1, 539.11, 539.12, 286.07; 600/300, 301; 128/903, 904
See application file for complete search history.

(56) References Cited

U.S. PATENT DOCUMENTS

| | | | |
|---|---|---|---|
| 6,057,758 A * | 5/2000 | Dempsey et al. | 340/539.12 |
| 2005/0151640 A1 * | 7/2005 | Hastings | 340/539.11 |
| 2007/0229249 A1 * | 10/2007 | McNeal | G08B 25/006 340/524 |
| 2008/0004904 A1 * | 1/2008 | Tran | 705/2 |
| 2008/0126132 A1 * | 5/2008 | Warner et al. | 705/3 |
| 2008/0221399 A1 * | 9/2008 | Zhou et al. | 600/301 |
| 2009/0099866 A1 * | 4/2009 | Newman | 705/2 |
| 2009/0275807 A1 * | 11/2009 | Sitzman | A61B 5/0205 600/301 |
| 2012/0065477 A1 * | 3/2012 | Enomoto | 600/300 |
| 2013/0214910 A1 * | 8/2013 | Bittner et al. | 340/12.22 |

* cited by examiner

*Primary Examiner* — Hung T Nguyen

(57) ABSTRACT

A patient monitoring secondary alarm notification system comprises a plurality of devices, configured to generate an alarm data, and a central station. The central station comprises a processor configured to receive the alarm data from the plurality of devices and monitor a plurality of dynamic conditions. The processor is further configured to assess the alarm data and the dynamic conditions to determine an alarm notification.

13 Claims, 2 Drawing Sheets

SYSTEM AND METHOD FOR MANAGING PATIENT MONITORING ALARMS

BACKGROUND OF THE INVENTION

The subject matter disclosed herein relates to patient monitoring. In particular, the present invention relates to managing a patient monitoring secondary alarm notification system.

Patient monitoring devices, such as devices monitoring patient physiological parameters, including but not limited to blood pressure, temperature and electrocardiogram ("ECG"), are designed to identify physiological problems experienced by the patient and to alert clinicians to those problems. Typically, clinicians are alerted to such problems via the generation of alarms, including primary auditory or visual alarms at the particular device. Secondary alarm notifications are generated in order to notify caregivers that are not in close proximity to the alarming device. These secondary alarms are often sent pagers, phones or smart devices carried by clinicians, or directly to sign boards. Primary and secondary alarms may also be generated by patient monitors when technical problems occur with the monitor itself, such as low battery, disconnection of patient monitoring lead, etc.

Current patient monitoring secondary alarm management systems typically follow static, pre-assigned rule sets. These systems do not, for example, take into account whether the first level or primary responder has recently received an alarm notification from a device or is already responding to an alarm notification from a different device, or numerous other conditions. Additionally, while a responder or clinician may desire to attend to all alarm events, he or she may be unable to respond to alarm events in a timely manner because his or her workflow is too heavy, or he or she is located too far away. Several alarms from different devices and locations may occur at once or within a short period of time, and/or a hospital floor may be understaffed, which may create a scenario in which it is impossible for a single responder or clinician to respond to all alarm events in a timely manner.

Hazards may arise when alarms go unrecognized or are not sent to the proper clinician for response. Unheeded alarms and slow response to alarms negatively affect patient care, and can lead to undesired outcomes for patients as an alarm event may indicate a deterioration of a patient's physiological condition, which often requires immediate attention.

Therefore, an improved method and system are needed for effectively managing a patient monitoring alarm notification system.

BRIEF DESCRIPTION OF THE INVENTION

The above-mentioned shortcomings, disadvantages and problems are addressed herein which will be understood by reading and understanding the following specification.

In an embodiment, a patient monitoring secondary alarm notification system comprises a plurality of devices configured to generate an alarm data and a central station. The central station comprises a processor configured to receive the alarm data from the plurality of devices and monitor a plurality of dynamic conditions. The processor is further configured to assess the alarm data and the dynamic conditions to determine an alarm notification.

In another embodiment, a method for managing a patient monitoring secondary alarm notification system comprises receiving at a central station an alarm data from a device and a plurality of dynamic conditions. The method further comprises assessing with a processor the plurality of dynamic conditions and the alarm data, and determining with a processor an alarm notification based on the plurality of dynamic conditions and the alarm data.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
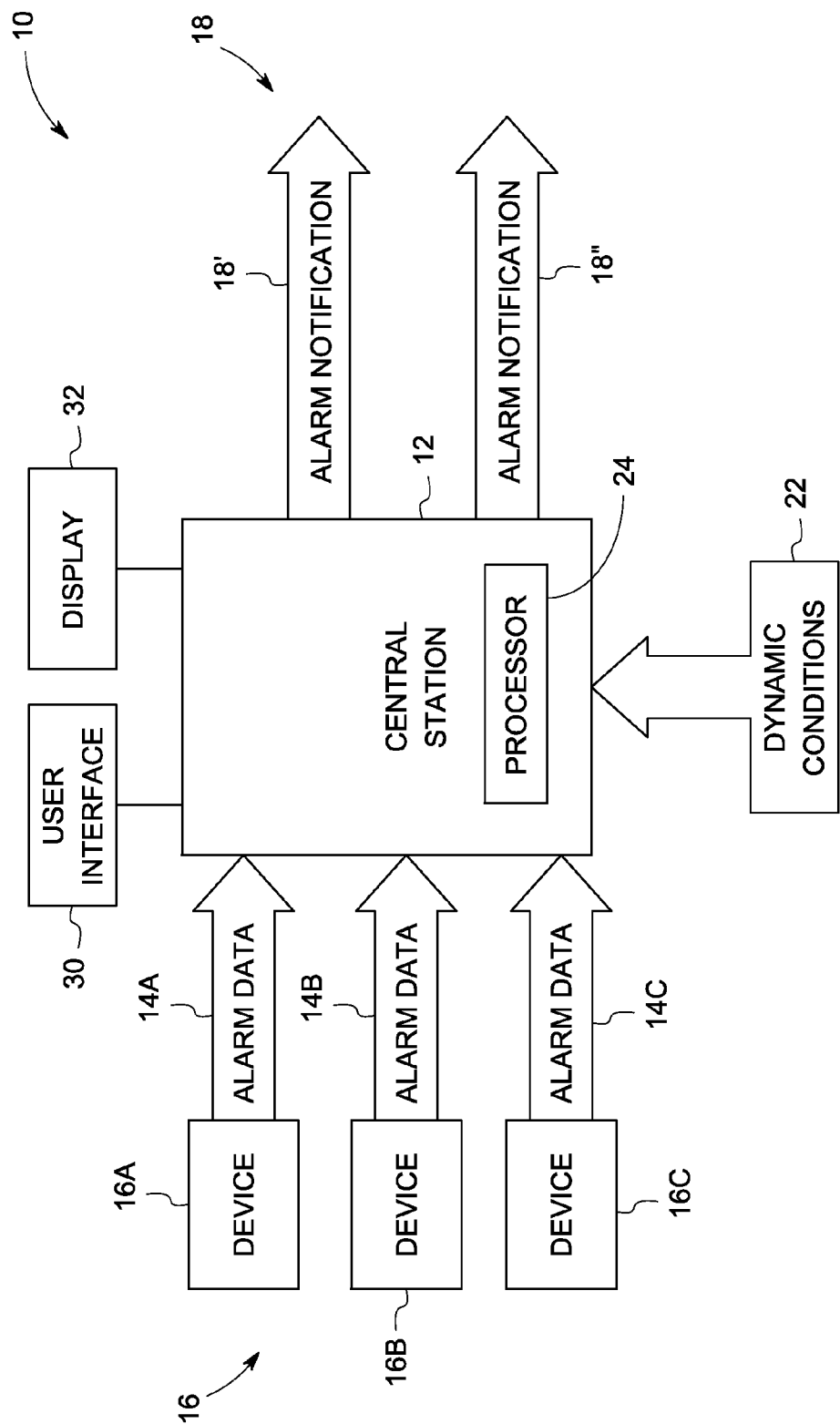
FIG. 1 is a schematic of an embodiment of an alarm notification system.

Referring to FIG. 1, a monitoring system 10 may comprise a plurality of devices 16 configured to generate alarm data 14. In one embodiment, a device 16A is a patient monitor and is configured to collect physiological data from a patient and generate alarm data 14A. Additionally, a device 16B is a nurse call system configured to generate alarm data 14B. Further, a device 16C is a lab system configured to generate alarm data 14C. It should be appreciated, however, that other types of devices configured to generate alarm data, as well as different combinations of such devices, may be envisioned. For example, the device 16 may be a radiology system, an electronic medical record system, an order entry system, a security system or a desktop messaging system. Moreover, the plurality of devices may be of the same type.

The alarm data 14 may comprise an alarm event and an alarm condition. For example, in one embodiment the patient monitor 16A collects physiological data from a patient and generates the alarm event 14A upon detection of a parameter outside a predefined range. In another example, the patient monitor 16A generates the alarm event 14A upon detection of an arrhythmia event. In yet another example, the patient monitor 16A may generate the alarm event 14A if it encounters a technical problem, such as a low battery or disconnection of patient monitoring lead, which needs to be remedied by a clinician or other staff member.

The alarm condition comprises information relating to the generation of the alarm event. For example, the alarm condition may comprise data related to an alarm severity, an alarm type or an alarm system, or any combination thereof.

The alarm severity is a rating related to the criticality of the alarm event, and may be rated, for example, in a low, medium or high type system, or with a numerical rating system. It should be appreciated, however, that other methods of rating the criticality of the alarm may be envisioned.

The alarm type comprises a description of the alarm. For example, in one embodiment the alarm type may be a parameter limit alarm or an arrhythmia alarm. In another embodiment, the alarm type may be a technical alarm related to an equipment state. In yet another embodiment, the alarm type may be a security alarm, such as those related to child abduction, a lab result alarm, or a nurse call alarm.

The alarm system may comprise an identification of the device 16 that generated the alarm data 14. For example, the alarm system may be a unique identifier for the patient monitor 16A, the nurse call system 16B, or the lab system 16C, or whatever other device 16 generated the alarm data 14. For example, in one embodiment, the patient monitor 16A would be identified by a serial number. In another embodiment, the patient monitor 16A would be identified by a care setting such as a room number or bed number. In yet another embodiment, the patient monitor 16A would be identified by a patient number.

The monitoring system 10 may further comprise a central station 12 connected to the plurality of devices 16. The central station 12 may comprise a processor 24. The processor 24 may be configured to receive the alarm data 14 generated by the plurality of devices 16. The processor 24 may also be configured to receive and/or monitor a plurality of dynamic conditions 22. The dynamic conditions 22 may comprise environmental conditions, responder conditions, or a combination thereof.

Environmental conditions may, for example, comprise data relating to a time of day, a shift schedule, and a unit alarm state. The time of day may be a reading based on Greenwich Mean Time (GMT) or Coordinated Universal Time (UTC) convention systems, or a system offset by time zones. It should be appreciated, however, that other time systems may be envisioned. For example, the time of day may be a more general morning, afternoon, evening, or night designation. In another embodiment, the time of day designation may be am or pm. The shift schedule may comprise a staffing schedule, possibly including time windows designated for shift changes. The unit alarm state may comprise a survey of at least a subset of the plurality of devices 16, in a specified location such as a unit or ward, to determine the number of devices generating alarm data at a particular time or within a particular time period. For example, in one embodiment, the alarm state may comprise the number of alarm events within the last thirty minutes in the ICU. In another embodiment, the unit alarm state may comprise the number of current alarm events in a care unit.

Responder conditions may comprise data relating to responder role, responder status, responder response frequency, responder location, responder resource status, or a combination thereof. The responder role may comprise a designation such as primary responder, secondary responder, or backup responder, or a title such as RN, CRN, technician, or clinician, or a combination thereof. Responder status may comprise an indication whether the responder is currently responding to an alarm. Responder response frequency is a count of the number of alarms the responder has responded to over a pre-defined time period. Responder location is an indication of where a responder is located in the hospital or care setting. Responder resource status is an indication of the responder availability. Responder location may be automatically tracked for each responder that is available in a given facility using RFID sensors or other commercially available tracking technologies.

The processor 24 may be further configured to assess the alarm data 14 and the dynamic conditions 22 using a rule-based engine and determine appropriate alarm notifications 18 shown in the embodiment of FIG. 1 as notifications 18' and 18" based on the alarm data 14 and the changing dynamic conditions 22. Each alarm notification 18 may comprise a responder identity, a transmission method, or a combination thereof. The responder identity may be a unique identifier or based on an association with the alarming device 16. For example, in one embodiment, the responder identify may be an employee identification number. In another embodiment, it may be based on the alarming device and its association with a patient room or bed number. In a further embodiment, it may be a designation such as primary responder, secondary responder, or backup responder, or a title such as RN, CRN, technician, or clinician, or a combination thereof. The transmission method may comprise an auditory broadcast, a display on a sign board or display, or a communication via an phone, a smart device, a pager, or spread-spectrum telecommunication, or any combination thereof. It should be appreciated that other known transmission methods may be envisioned. Optionally, the alarm notification 18 may further comprise an informational notification intended for bypassed responders. For example, if the alarm notification 18 is transmitted to the secondary responder for a given patient or event, an informational notification would be sent to the primary responder, apprising them of the alarm data 14 and the deviation in typical routing.

The monitoring system 10 may also comprise a user interface 30. The user interface 30 may be connected to the central station 12, and in one embodiment may be configured to allow a user to select a plurality of dynamic conditions to monitor. For example, a user may choose to monitor a subset of available environmental conditions and responder conditions. In another embodiment, the user interface 30 may be configured to receive an acknowledgement from a user. For example, a responder may acknowledge the alarm notification 18 via the user interface 30. The user interface 30 may comprise a trim knob, a series of hard buttons, a plurality of keys forming a keyboard, a touch screen, or some combination thereof. It should be appreciated, however, that other types of user interfaces may be envisioned.

The monitoring system 10 may also comprise a display 32. The display 32 may be connected to the central station 12 and configured to display information received from the plurality of devices 16, dynamic conditions 22, alarm notifications 18, or any combination thereof.

The monitoring system 10 is aimed at avoiding alarm roll-over, and increasing the likelihood that an appropriate, available responder will be notified. For example, if, for a given patient, the primary responder is located in a non-proximate care setting, and the secondary responder is currently responding to another alarm notification, then the tertiary responder will be notified of the alarm event.

Figure 2:
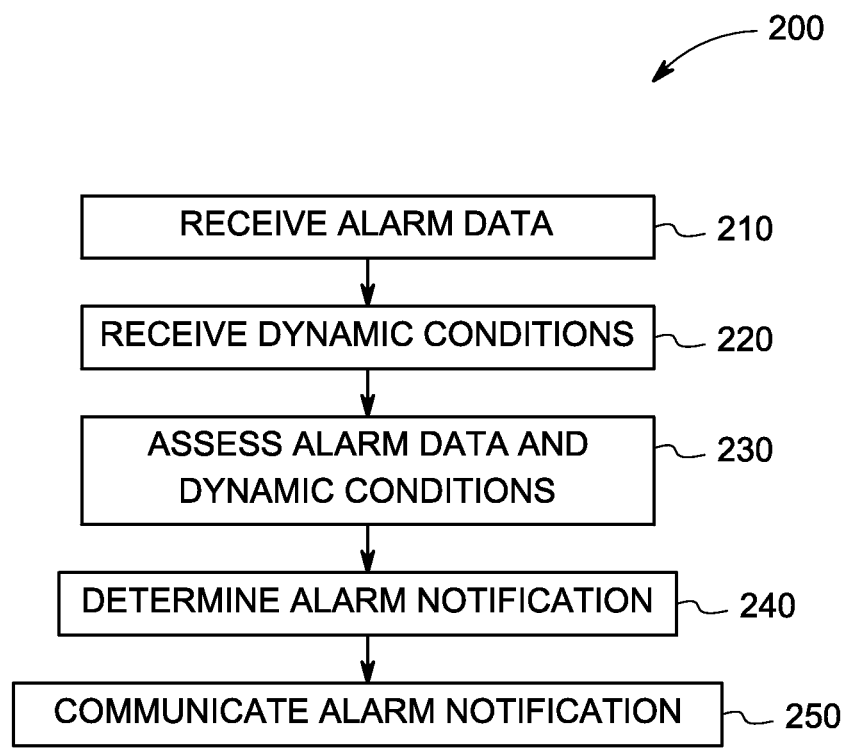
FIG. 2 is a flowchart of the steps performed in an exemplary method for managing a patient monitoring alarm notification system.

Having described the components of the monitoring system 10, an exemplary method of managing patient monitoring alarms 200 will now be described in connection with the flowchart depicted in FIG. 2. The method 200 may include a step 210 comprising receiving at the central station 12 the alarm data 14 from the respective device 16. The alarm data 14 may include information regarding the alarm event, including the type of alarm that generated the event, the criticality or severity of the condition that generated the alarm, and/or the type of device the alarm is generated therefrom.

The method 200 may also include a step 220, wherein the central station 12 also receives a plurality of dynamic conditions 22. The plurality of dynamic conditions 22 may comprise environmental conditions, responder conditions, or a combination thereof. The environmental condition may comprise at least one of an alarm location, a time of day and a unit alarm state. The responder condition may comprise at least one of responder role, responder status, responder response frequency, responder location and responder resource status.

The method 200 may also include a step 230, wherein the alarm data 14 and the plurality of dynamic conditions 22 are assessed by the processor 24. In an embodiment, the monitoring system 10 may be selectively configurable based on user input. While the central station 12 is configured to monitor a plurality of dynamic conditions 22, a selected subset of the plurality of dynamic conditions 22 may be assessed to determine the alarm notification 18. Therefore, the method 200 may also further comprise a step wherein a plurality of dynamic conditions 22 are selected with the user interface 30.

The method 200 may include a step 240 comprising determining with a processor the alarm notification 18 based on the plurality of dynamic conditions 22 and alarm data 14. The alarm notification 18 may comprise a responder identity, a transmission method, or a combination thereof.

The method 200 may further comprise a step 250 of communicating the alarm notification to a responder. In one embodiment, the communication may comprise displaying the alarm on the display 32. In another embodiment, the alarm may be communicated to a responder via an auditory broadcast, a display on a sign board, or a communication via a phone, a smart device, a pager or spread-spectrum telecommunication, or any combination thereof. Other types and methods of communication known to persons skilled in the art may be used, such as e-mails and pager notifications.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A patient monitoring secondary alarm notification system, comprising:
   a plurality of devices configured to generate an alarm data, and
   a central station comprising a processor configured to:
   receive the alarm data from the plurality of devices,
   monitor a plurality of dynamic conditions comprising a responder condition, an alarm location, and a unit alarm state, and wherein the unit alarm state comprises a number of alarm events in a unit during at least one of a particular time and a time period, and
   determine an alarm notification, based on the alarm data and the dynamic conditions, the alarm notification comprising a responder identity.

2. The patient monitoring secondary alarm notification system of claim 1, wherein the alarm data comprises an alarm event and an alarm condition.

3. The patient monitoring secondary alarm notification system of claim 1, wherein the alarm condition comprises at least one of severity, type and system.

4. The patient monitoring secondary alarm notification system of claim 1, wherein the responder condition comprises at least one of responder role, responder status, responder frequency, responder location, and responder resource status.

5. The patient monitoring secondary alarm notification system of claim 1, wherein the device is at least one of a patient monitor, a nurse call system, a lab system, a security system and an electronic medical record system.

6. The patient monitoring secondary alarm notification system of claim 1, wherein the alarm notification further comprises a transmission method.

7. The patient monitoring secondary alarm notification system of claim 1, further comprising a user interface configured to select the plurality of dynamic conditions.

8. A method for managing a patient monitoring secondary alarm notification system, the method comprising:
   receiving at a central station an alarm data from a device,
   receiving at the central station a plurality of dynamic conditions comprising an environmental condition and a responder condition, wherein the environmental condition comprises a unit alarm state, wherein the unit alarm state comprises a number of alarm events in a unit during at least one of a particular time and a time period,
   assessing with a processor the plurality of dynamic conditions and the alarm data, and
   determining with a processor an alarm notification based on the plurality of dynamic conditions and the alarm data, wherein the alarm notification comprises a responder identity.

9. The method of claim 8, further comprising:
   communicating the alarm notification to a responder.

10. The method of claim 8, wherein the environmental condition further comprises at least one of an alarm location and time of day.

11. The method of claim 8, wherein the responder condition comprises at least one of responder role, responder status, responder response frequency, responder location, and responder resource status.

12. The method of claim 8, wherein the device is a patient monitor.

13. The method of claim 8, further comprising:
   selecting the plurality of dynamic conditions with a user interface.

* * * * *